United States Patent
Drescher et al.

(10) Patent No.: US 6,306,784 B1
(45) Date of Patent: *Oct. 23, 2001

(54) ALKALI SILICATE GLASS

(75) Inventors: Helga Drescher, Feldkirch; Martin Frank, Schaan; Volker Rheinberger, Vaduz; Wolfram Höland, Schaan, all of (AT)

(73) Assignee: Ivoclar AG (LI)

( * ) Notice: Subject to any disclaimer, the term of this patent is extended or adjusted under 35 U.S.C. 154(b) by 0 days.

This patent is subject to a terminal disclaimer.

(21) Appl. No.: 09/590,978

(22) Filed: Jun. 9, 2000

Related U.S. Application Data

(63) Continuation of application No. 09/097,189, filed on Jun. 12, 1998, now Pat. No. 6,121,175
(60) Provisional application No. 60/063,236, filed on Oct. 23, 1997.

(30) Foreign Application Priority Data

Jun. 12, 1997 (DE) .............................................. 197 25 552

(51) Int. Cl.$^7$ .......................... C03C 3/091; A61K 6/033; A61K 6/00
(52) U.S. Cl. ................................ 501/59; 501/67; 501/68; 501/69; 501/70; 501/72; 501/66; 501/3; 501/16; 501/21; 501/24; 501/25; 501/26; 106/35; 433/206; 433/212.1; 433/202.1; 427/2.26; 427/2.27; 427/2.29
(58) Field of Search ........................... 106/35; 433/202.1, 433/206, 212.1; 427/2.26, 2.27, 2.29; 428/426, 428; 501/68, 70, 69, 66, 67, 72, 89, 3, 16, 21, 24, 25, 26

(56) References Cited

U.S. PATENT DOCUMENTS

| | | | |
|---|---|---|---|
| 4,604,366 | 8/1986 | Kacicz et al. | 501/6 |
| 4,772,436 | 9/1988 | Tyszblat | 264/19 |
| 5,562,733 | 10/1996 | Weissbach et al. | 433/201.1 |
| 5,641,347 | 6/1997 | Grabowski et al. | 106/35 |
| 5,713,994 | * 2/1998 | Kramer et al. | 106/35 |
| 6,121,175 | * 9/2000 | Drescher et al. | 501/59 |

FOREIGN PATENT DOCUMENTS

| | | |
|---|---|---|
| 40 20 893 A1 | 1/1971 | (DE) . |
| 30 39 930 A1 | 5/1981 | (DE) . |
| 0 695 726 A1 | 2/1996 | (EP) . |
| 0 827 941 A1 | 3/1998 | (EP) . |
| 53-31716 | 3/1978 | (JP) . |
| 1-212248 | * 8/1989 | (JP) . |

* cited by examiner

*Primary Examiner*—C. Melissa Koslow
(74) *Attorney, Agent, or Firm*—Nixon Peabody LLP

(57) ABSTRACT

Alkali silicate glasses are described which, in view of their good chemical stability and their optical properties and processing properties, are particularly suitable as a coating or veneering material for ceramic dental frameworks and hence for the production of all-ceramic dental restorations such as crowns or bridges.

14 Claims, No Drawings

ALKALI SILICATE GLASS

This application claims the benefit of U.S. Provisional Patent Application Ser. No. 60/063,236, filed Oct. 23, 1997.

This application is a continuation of U.S. application Ser. No. 09/097,189, filed Jun. 12, 1998, now U.S. Pat. No. 6,121,175.

The invention relates to alkali silicate glass and, in particular, to such a glass which is suitable for adjusting in a desired manner the optical properties and processing properties of coating and veneering material for ceramic dental restorations.

In addition to metallic dental restorations which are veneered with ceramic layers for aesthetic reasons, all-ceramic restorations are increasingly being used in dentistry wherein a ceramic veneering or coating material is applied to a core of ceramic material. Inter alia glass ceramics are suitable for use as both core and coating material.

The optical properties in particular, and the processing properties of glass ceramic coating material are, however, often unsatisfactory. The glass ceramics used exhibit considerable cloudiness due to their high crystal content which is not acceptable, particularly for dental restorations for the incisor region. Moreover, the glass ceramics have a very high expansion coefficient in many cases, for which reason they are unsuitable as a coating material for cores of glass ceramic with a low expansion coefficient, such as lithium disilicate glass ceramic. As a result of the unsatisfactory adjustment of the expansion coefficients, undesired detachment of the coating material may occur.

It is also known that leucite-containing glass ceramics in particular have very high thermal expansion coefficients. These are attributable to the content of leucite crystals which are formed by controlled crystallisation of an appropriate starting glass.

Alkali silicate glasses are known from EP-A-695 726 which are suitable for veneering primarily metallic dental frameworks and contain no $B_2O_3$. During heat treatment at temperatures of 600° C. to 1000° C. and hence under conventional conditions for further dental processing, the glasses, however, form corresponding glass ceramics which, as a result of their crystal content, are very cloudy and are therefore unsuitable for obtaining a high translucence in a glass ceramic coating material. The crystal content, particularly leucite, also leads to undesirably high expansion coefficients and sintering temperatures, so that they are unsatisfactory for veneering ceramic substrates with low expansion coefficients.

The object of the invention is, therefore, to provide a glass which does not crystallise under the conventional conditions of dental processing in the temperature range from 600° C. to 1000° C., has a low thermal expansion coefficient, a low sintering temperature, good chemical stability and high translucence, and consequently may be added in particular to dental glass ceramic coating material in order to improve the properties thereof.

The alkali silicate glass according to the invention is characterised in that it contains the following components:

| Component | Wt. % |
|---|---|
| $SiO_2$ | 55.0 to 71.0 |
| $Al_2O_3$ | 5.0 to 16.0 |
| $B_2O_3$ | 0.2 to 10.0 |
| $K_2O$ | 4.5 to 10.0 |
| $Na_2O$ | 3.0 to 14.0 |

$SiO_2$ is preferably present in an amount of 55.0 to 65.0 wt. %. The glass according to the invention may additionally contain at least one of the following components:

| Component | Wt. % |
|---|---|
| CaO | 0 to 3.0 |
| F | 0 to 3.0 |
| $P_2O_5$ | 0 to 0.6 |
| $Li_2O$ | 0 to 4.0 |
| BaO | 0 to 5.0 |
| ZnO | 0 to 4.0 |
| $TiO_2 + ZrO_2$ | 0.2 to 5.0 |
| $CeO_2$ | 0 to 2.0 |

With the exception of $TiO_2$ and $ZrO_2$, the lower limits for these additional components are usually 0.05 wt. %.

Preferred quantity ranges exist for the individual components of the alkali silicate glass according to the invention. These may be chosen independently of one another and are as follows:

| Component | Wt. % |
|---|---|
| $SiO_2$ | 60.0 to 65.0 |
| $Al_2O_3$ | 6.0 to 10.0 |
| $B_2O_3$ | 0.5 to 8.1 |
| $K_2O$ | 5.5 to 9.0 |
| $Na_2O$ | 3.5 to 10.0 |
| CaO | 0.5 to 3.0 |
| F | 0.2 to 2.0 |

Particularly preferred quantity ranges for the individual components of the glass according to the invention are as follows and these may be chosen independently of one another:

| Component | Wt. % |
|---|---|
| $SiO_2$ | 61.0 to 64.0 |
| $Al_2O_3$ | 7.0 to 9.0 |
| $B_2O_3$ | 0.5 to 4.0 |
| $Na_2O$ | 7.0 to 9.0 |
| CaO | 0.5 to 1.5 |
| F | 1.0 to 2.0 |
| $Li_2O$ | 0 to 3.0 |
| BaO | 1.5 to 3.5 |
| ZnO | 2.0 to 3.5 |

All the above-mentioned quantities in wt. % relate to the glass.

For the production of the glass according to the invention, it is preferable to proceed in such a way that suitable starting materials, such as carbonates, oxides and fluorides, are melted at temperatures from 1350° C. to 1650° C., preferably 1400° C. to 1600° C. over a period of 30 minutes to 4 hours, preferably one hour to 2.5 hours, with the formation of a homogeneous melt. The molten glass is then usually quenched in water i.e. fritted and, after drying, ground to the desired particle size.

It was possible to ascertain by scanning electron microscope analyses that the glass according to the invention is free from crystals. Additionally, it became apparent that the glass also withstands the conditions prevailing during conventional further dental processing by sintering without the formation of crystals which occurs with known glasses. Crystallisation did not occur even during a heat treatment at temperatures of 600° C. to 1000° C. for one minute to 2 hours.

This behaviour is presumably attributable to the special composition of the glass according to the invention.

The glass according to the invention usually has a sintering temperature of 650° C. to 1150° C. Glasses having a sintering temperature of 700° C. to 1050° C. are particularly preferred. Glass which can be sintered at low temperatures of 750° C. to 880° C. and can thus be processed is quite particularly preferred.

A rate of heating of 3 to 100° C./min and preferably 30 to 80° C./min and a holding time at the sintering temperature of 10 seconds to 1 hour and preferably 30 seconds to 5 minutes is usually chosen for carrying out sintering. It is advantageous to carry out sintering under vacuum so that the sintered body has a few pores as possible.

The thermal expansion coefficient of the glass according to the invention is usually 5.5 to $12.5 \times 10^{-6} K^{-1}$, preferably 6.0 to $11.0 \times 10^{-6} K^{-1}$, measured in the temperature interval of 100° C. to 400° C.

The glass according to the invention is used by itself or together with other components preferably as dental material.

To this end it is generally used in the form of a powder with an average particle size of less than 90 μm. Further suitable components are glass ceramics and other glasses, but also dyes, particularly coloured pigments, oxides of the 3d elements or metal colloids, and fluorescent materials, particularly ytterbium silicate doped with d and f elements.

Dental material which contains at least one apatite glass ceramic as the further component is particularly advantageous.

A preferred apatite glass ceramic is one containing CaO, $P_2O_5$ and F in a molar ratio of $CaO:P_2O_5:F$ of 1:0.020 to 1.5:0.03 to 4.2 and contains apatite crystals as the main crystal phase. Such apatite glass ceramics are characterised by particularly good chemical stability, which is of great importance especially for use in dental restorations.

Moreover, the use of an apatite glass ceramic which contains at least one of the following components and contains apatite crystals as the main crystal phase is also preferred:

| Component | Wt. % |
|---|---|
| $SiO_2$ | 45.0 to 70.0 |
| $Al_2O_3$ | 5.0 to 22.0 |
| $P_2O_5$ | 0.5 to 6.5 |
| $K_2O$ | 3.0 to 8.5 |
| $Na_2O$ | 4.0 to 13.0 |
| CaO | 1.5 to 11.0 |
| F | 0.1 to 2.5 |

In particular preference, this apatite glass ceramic additionally contains at least one of the following components:

| Component | Wt. % |
|---|---|
| $B_2O_3$ | 0 to 8.0 |
| $La_2O_3$ | 0 to 5.0 |
| $Li_2O$ | 0 to 5.0 |
| BaO | 0 to 5.0 |
| MgO | 0 to 5.0 |
| ZnO | 0 to 5.0 |
| SrO | 0 to 7.0 |
| $TiO_2$ | 0 to 4.0 |
| $ZrO_2$ | 0 to 4.0 |
| $CeO_2$ | 0 to 3.0 |

The above amounts given in wt. % relate to the apatite glass ceramic.

The apatite glass ceramics described above are produced by melting a starting glass composed of suitable starting materials, such as oxides, carbonates and fluorides, at temperatures of 1200° C. to 1650° C., pouring this into water and subjecting the glass granules formed, optionally after further comminution, to a heat treatment at temperatures of more than 900° C. and up to 1200° C. for a period of 30 minutes to 6 hours.

The apatite glass ceramics obtained are characterised by high translucence, good chemical stability and a low expansion coefficient. These properties are presumably attributable to their special composition and to the apatite crystals produced during their manufacture, which crystals have in particular a needle-shaped morphology and hence resemble the apatite crystals of natural tooth material.

The dental material according to the invention normally has a thermal expansion coefficient of 5.5 to $12.5 \times 10^{-6} K^{-1}$, measured in the temperature range of from 100 to 400° C. The coefficient required in each case can be adjusted by a suitable choice of the type of alkali silicate glass and any other components and the quantities thereof. Favourable dental materials contain 10 to 90 wt. % of alkali silicate glass and 90 to 10 wt. % of other components, based on the dental material.

The dental material is suitable for coating substrates and in particular for coating or veneering dental restorations. Coating is effected in particular by applying the dental material to the chosen substrate and then sintering it at temperatures of 650 to 1150° C.

In preference, a powder of the glass according to the invention is mixed with a powder of the other components optionally present and processed to a paste by adding aqueous mixing solutions. This paste is then applied to a substrate and, after the desired shaping, sintering takes place to obtain a firmly adhering coating or veneer.

The dental material according to the invention may be used as a coating or veneering material for substrates such as dental frameworks, based on ceramic or glass ceramic materials. In view of its low expansion coefficient, it is used preferably with substrate materials with a thermal expansion coefficient of 7.0 to 12.0, particularly 8.0 to $11.0 \times 10^{-6} K^{-1}$. It is used preferably for coating or veneering $ZrO_2$ ceramics, $Al_2O_3$ ceramics, $ZrO_2/Al_2O_3$ ceramics, ceramic or glass ceramic composite materials and titanium.

It is used particularly advantageously, however, for veneering substrates based on lithium disilicate glass ceramic in order to produce in this way aesthetically very attractive fully ceramic dental products which have very high strength and excellent chemical stability.

Lithium disilicate glass ceramics having the following composition which may be obtained e.g. by melting appropriate starting glasses, fitting and heat treatment at 400° C. to 1100° C. have proved to be particularly suitable:

| Component | Wt. % |
|---|---|
| $SiO_2$ | 57.0 to 80.0 |
| $Al_2O_3$ | 0 to 5.0 |
| $La_2O_3$ | 0.1 to 6.0 |
| MgO | 0 to 5.0 |
| ZnO | 0 to 8.0 |
| $K_2O$ | 0 to 13.5 |
| $Li_2O$ | 11.0 to 19.0 |
| $P_2O_5$ | 0 to 11.0 | with the proviso that
(a) $Al_2O_3+La_2O_3$ is 0.1 to 7.0 wt. % and
(b) MgO+ZnO is 0.1 to 9.0 wt. %.

The amounts given in wt. % are based on the lithium disilicate glass ceramic.

For the production of coatings, dental material according to the invention that has a thermal expansion coefficient that is smaller than that of the substrate to be coated is advantageous. Dental material whose expansion coefficient is not more than $3.0 \times 10^{-6} K^{-1}$ smaller than that of the substrate is particularly advantageous.

The alkali silicate glass according to the invention and the dental material according to the invention may be processed in the usual way together with the additives optionally present to obtain shaped dental products. Suitable shaped dental products according to the invention containing the alkali silicate glass or the dental material are, in particular, dental restorations such as an inlay, an onlay, a bridge, an abutment, a jacket, a veneer, a facet, a filling, or a connector.

Particularly preferred dental restorations are bridges, crowns and partial crowns.

The dental products preferably have a core based on ceramic or glass ceramic material, particularly lithium disilicate glass ceramic, onto which the glass according to the invention or the dental material according to the invention is applied.

Preferred lithium disilicate glass ceramics have already been described above.

In contrast to conventional glass, crystallisation which would undesirably lower its translucence does not occur with the glass according to the invention under the conditions prevailing during the sintering thereof. It therefore reproduces essentially the colour of the coated substrate which is very desirable, particularly during the production of all-ceramic dental restorations.

The lack of crystal formation and in particular the lack of formation of leucite crystals ascertained in the case of known glasses is a particular advantage since the high expansion coefficient of leucite would confer a high thermal expansion coefficient on the glass. The glass would therefore be unsuitable for coating substrates with low expansion coefficients, such as $ZrO_2$ or lithium disilicate glass ceramic. The lack of adjustment of the expansion coefficients would lead to high stresses which regularly manifest themselves in cracks and chippings. These disadvantages are not exhibited by the glass according to the invention due to its low expansion coefficient, so it is very suitable for coating substrates with low expansion coefficients.

Moreover, despite its $B_2O_3$ content, the glass exhibits excellent chemical stability which is vital for its use as a dental material, which is permanently flushed by acid fluids in the oral cavity.

Finally, the glass may be sintered onto a substrate within a short sintering time even at low temperatures in order to produce a firmly adhering coating or veneer in this way.

Admixing the glass with apatite glass ceramics in particular leads to dental materials which have increased translucence, a shorter sintering time and lower sintering temperature and a lower thermal expansion coefficient compared with the pure apatite glass ceramic.

The invention will be explained in more detail below on the basis of examples.

EXAMPLES

Examples 1 to 8

A total of 8 different glasses according to the invention with the chemical compositions given in Table I were produced.

TABLE 1

Compositions of glasses according to the invention (quantities in wt. %)

| Ex. No. | $SiO_2$ | $Al_2O_3$ | $P_2O_5$ | CaO | F | $K_2O$ | $Na_2O$ | $Li_2O$ | $B_2O_3$ | $TiO_2$ | $ZrO_2$ | $CeO_2$ | BaO | ZnO |
|---|---|---|---|---|---|---|---|---|---|---|---|---|---|---|
| 1 | 56.5 | 6.7 | 0.3 | 3.0 | 0.9 | 8.6 | 6.6 | 1.4 | 4.0 | — | 2.5 | 1.0 | 4.7 | 3.8 |
| 2 | 61.5 | 8.7 | — | 1.0 | 1.7 | 7.0 | 8.8 | — | 2.4 | 1.5 | 1.0 | 0.5 | 2.9 | 3.0 |
| 3 | 60.4 | 11.9 | — | — | 0.3 | 6.4 | 7.0 | 1.8 | 0.3 | 1.5 | 3.5 | — | 3.2 | 3.7 |
| 4 | 61.4 | 8.5 | — | 1.1 | 1.7 | 7.8 | 8.7 | 0.6 | 1.9 | 1.5 | 1.0 | 0.5 | 2.1 | 3.2 |
| 5 | 62.3 | 8.7 | — | 1.3 | 1.6 | 7.0 | 7.0 | 2.0 | 1.1 | 1.4 | 1.0 | 0.6 | 3.0 | 3.0 |
| 6 | 70.8 | 8.6 | — | 2.1 | 0.9 | 6.9 | 8.3 | 1.5 | 0.2 | 0.7 | — | — | — | — |
| 7 | 63.4 | 6.2 | 0.4 | 1.7 | — | 6.4 | 9.6 | — | 3.7 | 1.7 | 1.1 | 0.5 | 2.3 | 3.0 |
| 8 | 61.9 | 99 | — | 1.1 | 1.5 | 5.8 | 3.7 | 0.2 | 8.0 | 1.4 | 1.1 | 0.5 | 2.8 | 2.1 |

For the production of said glasses, an appropriate batch of suitable oxides, carbonates and fluorides in each case was melted in a platinum/rhodium crucible at a temperature of 1550° C. to 1600° C. for a homogenisation period of 1 to 1.5 hours. The glass melt was quenched in water, and the granules of the glass formed were dried and ground to an average particle size of less than 90 μm.

Selected properties that were determined on specimens composed of the respective glass are given in Table II. The examples illustrate how glasses with different properties may be obtained by altering the chemical composition.

TABLE II

| Ex. | Firing temperature [° C.]* | Tg [° C.] | α-value x $10^{-6} K^{-1}$ (100° C.– 400° C.) | Optical appearance | Acid resistance [μg/cm²] |
|---|---|---|---|---|---|
| 1 | 760 | 500 | 9.6 | translucent | 26 |
| 2 | 810 | 522 | 9.1 | very translucent | 17.2 |
| 3 | 880 | 528 | 9.5 | translucent | 17 |
| 4 | 770 | 494 | 9.4 | very translucent | 26.3 |
| 5 | 750 | 468 | 9.4 | very translucent | 17.9 |
| 7 | 840 | 565 | 8.9 | very translucent | 30 |
| 8 | 880 | 543 | 6.6 | very translucent | >100 |

*Firing temperature = temperature which was used for production of the specimens by sintering onto quartz (vacuum, 1 minute holding time)

Determination of the expansion coefficient α

In order to measure the thermal expansion coefficient α, a rod-shaped green compact was prepared from powder of the glass in question, and said compact was sintered in a vacuum furnace at a rate of heating of 60° C./min and with a holding time of 1 minute at the respective firing temperature. A glaze bake was then carried out without vacuum at a 20° C. higher final temperature and with a holding time of 1 minute. The thermal expansion coefficient was determined on the specimen obtained.

Determination of acid resistance

The acid resistance is a measure of the chemical stability of glasses and glass ceramics used in dentistry in particular, since these are permanently exposed to the action of acid substances in the oral cavity.

The acid resistance was determined according to the ISO specification 6872:1995. To this end, small sample plates 12 mm in diameter and 1 mm thick were prepared initially by sintering together glass granules with an average particle size of 90 μm. The granules were kept at the sintering temperature for 1 minute. The sample plates were then treated for 16 hours in a Soxhlet apparatus with 4 vol. % of aqueous acetic acid and finally the loss of mass occurring was determined as a measure of the acid resistance.

Example 9

This Example describes the use of glasses according to the invention according to Example 2 and 4 together with an apatite glass ceramic (A) as a coating material for ceramic frameworks and thus for the production of fully ceramic dental products.

The apatite glass ceramic (A) had the composition $SiO_2$ 55.5 wt. %, $Al_2O_3$ 19.2 wt. %, $P_2O_5$ 1.2 wt. %, CaO 2.7 wt. %, F 0.6 wt. %, $K_2O$ 6.7 wt. %, $Na_2O$ 9.7 wt. %, $B_2O_3$ 0.3 wt. %, $TiO_2$ 1.4 wt. %, $ZrO_2$ 1.2 wt. % and $CeO_2$ 0.5 wt. %. For the preparation thereof, a starting glass of the appropriate composition was melted, fritted and ground to a powder. This powder was then heat treated for one hour at 1020° C. The crystals present in the glass ceramic formed could be identified as needle-shaped apatite crystals by X-ray diffractometry.

In order to obtain a suitable expansion coefficient and sintering temperature, this apatite glass ceramic (A) was mixed with the alkali silicate glasses 2 and 4 according to the invention in the form of powders with an average particle size of less than 90 μm and in a weight ratio of 30% apatite glass ceramic (A), 35% alkali silicate glass according to Example 2 and 35% alkali silicate glass according to Example 4.

This mixture was sintered at 880° C. to a rod-shaped green compact in a vacuum furnace at a rate of heating at 60° C./min and with a holding time of 1 min. A thermal expansion coefficient of $9.5 \times 10^{-6} K^{-1}$, measured in the temperature range of from 100 to 400° C., was determined for the sample obtained.

This mixture could thus be used for sintering onto a substrate with a thermal expansion coefficient of $10.6 \times 10^{-6} K^{-1}$, such as lithium disilicate glass ceramic, at an advantageous processing temperature of 830+ C.

Processing on a tooth substrate can usually take place at temperatures that are 50 to 100° C. lower than the sintering temperature on quartz.

Example 10

In the same way as Example 9, different glasses according to the invention may be mixed together or with other glass ceramics to obtain desired expansion coefficients and sintering temperatures.

A powder mixture of 25 wt. % of alkali silicate glass according to Example 4 with 50 wt. % of apatite glass ceramic (B) (heat treatment at 1100° C.), and 25 wt. % of apatite glass ceramic (A) according to Example 9 (heat treatment 1020° C.) was prepared in order to obtain a dental material according to the invention with a low sintering temperature of 830° C. and an expansion coefficient of $9.5 \times 10^{-6} K^{-1}$. Such a material had outstanding optical properties and was highly suitable as a sintering ceramic for an all-ceramic framework structure with a low thermal expansion coefficient.

The apatite glass ceramic (B) used in this case had the composition $SiO_2$ 59.2 wt. %, $Al_2O_3$ 7.9 wt. %, $P_2O_5$ 3.0 wt. %, CaO 5.1 wt. %, F 0.6 wt. %, $K_2O$ 6.8 wt. %, $Na_2O$ 9.6 wt. %, $Li_2O$ 0.3 wt. %, $B_2O_3$ 1.0 wt. %, $TiO_2$ 1.5 wt. %, $ZrO_2$ 2.5 wt. %, $CeO_2$ 0.5 wt. % and $ZnO_2$ 2.0 wt. %. For the preparation thereof, a starting glass of the appropriate composition was melted, fritted and ground to a powder. This powder was then heat treated at 1100° C. in order to form the glass ceramic.

Examples 11 to 14

In these Examples, other mixtures of alkali silicate glasses according to the invention with apatite glass ceramics were examined, which are highly suitable as coating or veneering materials that can be sintered onto substrates with low thermal expansion coefficients.

The following apatite glass ceramics were used:
1. Apatite glass ceramic (B) according to Example 10
2. Apatite glass ceramic (C) having the composition:
   $SiO_2$ 62.8 wt. %, $Al_2O_3$ 13.1 wt. %, $P_2O_5$ 1.2 wt. %, CaO 2.7 wt. %, F 0.6 wt. %, $K_2O$ 6.3 wt. %, $Na_2O$ 5.9 wt. %, $ZrO_2$ 1.7 wt. %, $CeO_2$ 0.5 wt. %, BaO 1.8 wt. % and ZnO 3.4 wt. %.
3. Apatite glass ceramic (D) having the composition:
   $SiO_2$ 64.5 wt. %, $Al_2O_3$ 8.4 wt. %, $P_2O_5$ 1.1 wt. %, CaO 2.8 wt. %, F 0.7 wt. %, $K_2O$ 6.6 wt. %, $Na_2O$ 9.6 wt. %, $B_2O_3$ 2.2 wt. %, $TiO_2$ 1.2 wt. %, $ZrO_2$ 0.4 wt. %, and ZnO 2.5 wt. %.

The compositions of the individual mixtures and the heat treatment carried out for the production of the apatite glass ceramic used in each case are given in Table III.

The properties determined for these mixtures are also stated in Table III and they show that, by means of a suitable choice of components, it is possible to obtain dental materials with properties adjusted to the application in question.

TABLE III

Properties of mixtures of glasses according to the invention and apatite glass ceramics

| Ex. | Composition | Heat treatment [° C./h] | Mixing ratio [in wt. %] | Sintering temp. [° C.] | Tg [° C.] | α-value x $10^{-6} K^{-1}$ (100° C.– 400° C.) | Optical appearance | Acid resistance [μg/cm²] |
|---|---|---|---|---|---|---|---|---|
| 11 | Apatite glass ceramic (B) | 1050/1 | 50 | 850 | 530 | 9.3 | milky, cloudy, translucent | <100 |
|  | Alkali silicate glass 2 | — | 50 |  |  |  |  |  |

TABLE III-continued

Properties of mixtures of glasses according to the invention and apatite glass ceramics

| Ex. | Composition | Heat treatment [° C./h] | Mixing ratio [in wt. %] | Sintering temp. [° C.] | Tg [° C.] | α-value × $10^{-6}$ $K^{-1}$ (100° C.–400° C.) | Optical appearance | Acid resistance [μg/cm$^2$] |
|---|---|---|---|---|---|---|---|---|
| 12 | Apatite glass ceramic (B) | 1020/1 | 50 | 870 | 542 | 8.0 | milky, translucent | <100 |
|  | Alkali silicate glass 8 | — | 50 |  |  |  |  |  |
| 13 | Apatite glass ceramic (C) | 1000/1 | 40 | 910 | 552 | 8.8 | very translucent | <100 |
|  | Alkali silicate glass 5 | — | 60 |  |  |  |  |  |
| 14 | Apatite glass ceramic (D) | 1050/1 | 70 | 850 | 539 | 8.7 | slightly milky, slightly opal, translucent | <100 |
|  | Alkali silicate glass 6 | — | 30 |  |  |  |  |  |

What is claimed is:

1. An alkali silicate glass, which comprises the following components:

| Component | Wt. % |
|---|---|
| $SiO_2$ | 55.0 to 71.0 |
| $Al_2O_3$ | 5.0 to 16.0 |
| $B_2O_3$ | 0.2 to 10.0 |
| $K_2O$ | 4.5 to 10.0 |
| $Na_2O$ | 3.0 to 14.0 |
| $TiO_2 + ZrO_2$ | 0.2 to 5.0. |

2. A glass according to claim 1, which additionally comprises at least one of the following components:

| Component | Wt. % |
|---|---|
| CaO | 0 to 3.0 |
| F | 0 to 3.0 |
| $P_2O_5$ | 0 to 0.6 |
| $Li_2O$ | 0 to 4.0 |
| BaO | 0 to 5.0 |
| ZnO | 0 to 4.0 |
| $CeO_2$ | 0 to 2.0. |

3. A glass according to claim 1, wherein quantities of some components, independently of one another, are as follows:

| Component | Wt. % |
|---|---|
| $SiO_2$ | 60.0 to 65.0 |
| $Al_2O_3$ | 6.0 to 10.0 |
| $B_2O_3$ | 0.5 to 8.1 |
| $K_2O$ | 5.5 to 9.0 |
| $Na_2O$ | 3.5 to 10.0; | and further comprises the following components:

| Component | Wt. % |
|---|---|
| CaO | 0.5 to 3.0 |
| F | 0.2 to 2.0. |

4. A glass according to claim 1, wherein the quantities of some components, independently of one another, are as follows:

| Component | Wt. % |
|---|---|
| $SiO_2$ | 61.0 to 64.0 |
| $Al_2O_3$ | 7.0 to 9.0 |
| $B_2O_3$ | 0.5 to 4.0 |
| $Na_2O$ | 7.0 to 9.0; | and further comprises the following components:

| Component | Wt. % |
|---|---|
| CaO | 0.5 to 1.5 |
| F | 1.0 to 2.0 |
| $Li_2O$ | 0 to 3.0 |
| BaO | 1.5 to 3.5 |
| ZnO | 2.0 to 3.5. |

5. A glass according to claim 1, which does not crystallise during a heat treatment at temperatures from 600° C. to 1000° C. for one minute to 2 hours.

6. A glass according to claim 1, which has a sintering temperature of 650° C. to 1150° C.

7. A dental material, which comprises the glass according to claim 1.

8. A dental material according to claim 7, which has a linear thermal expansion coefficient of 5.5 to 12.5×$10^{-6}K^{-1}$, measured in the temperature range of from 100 to 400° C.

9. A shaped dental product, which comprises the alkali silicate glass according to claim 1.

10. A shaped dental product according to claim 9, which is a dental restoration.

11. A shaped dental product according to claim 9, which comprises a core comprising a ceramic or glass ceramic material and a coating applied to the core, wherein the coating comprises the alkali silicate glass.

12. A method of coating a substrate comprising:
providing a substrate and
coating the substrate with the dental material of claim 7.

13. A method according to claim 12, wherein the substrate is comprised of a ceramic or a glass ceramic.

14. A method according to claim 12, further comprising: sintering the coated substrate at temperatures of 650° C. to 1050° C.

* * * * *